United States Patent
Souza et al.

(10) Patent No.: US 10,301,274 B2
(45) Date of Patent: May 28, 2019

(54) CRYSTALLINE DERIVATIVES OF (S)-1-((2R,3R,4S,5S)-5-ALLYL-3-METHOXY-4-(TOSYLMETHYL)TETRAHYDROFURAN-2-YL)-3-AMINOPROPAN-2-OL

(71) Applicant: Sandoz AG, Basel (CH)

(72) Inventors: Fabio E. s. Souza, Mississauga (CA); Ricardo Orprecio, Etobicoke (CA); Ming Pan, Mississauga (CA)

(73) Assignee: Sandoz AG, Basel (CH)

( * ) Notice: Subject to any disclaimer, the term of this patent is extended or adjusted under 35 U.S.C. 154(b) by 54 days.

(21) Appl. No.: 15/123,310

(22) PCT Filed: Mar. 6, 2015

(86) PCT No.: PCT/CA2015/050168
§ 371 (c)(1),
(2) Date: Sep. 2, 2016

(87) PCT Pub. No.: WO2015/131286
PCT Pub. Date: Sep. 11, 2015

(65) Prior Publication Data
US 2017/0066735 A1    Mar. 9, 2017

Related U.S. Application Data

(60) Provisional application No. 61/948,875, filed on Mar. 6, 2014.

(51) Int. Cl.
| | |
|---|---|
| *C07D 307/02* | (2006.01) |
| *C07D 307/20* | (2006.01) |
| *C07C 69/76* | (2006.01) |
| *C07D 405/06* | (2006.01) |
| *C07D 413/06* | (2006.01) |

(52) U.S. Cl.
CPC .......... *C07D 307/20* (2013.01); *C07C 69/76* (2013.01); *C07D 405/06* (2013.01); *C07D 413/06* (2013.01)

(58) Field of Classification Search
CPC .. C07D 307/20; C07D 413/06; C07D 405/06; C07C 69/76
USPC ....................................................... 549/475
See application file for complete search history.

(56) References Cited

U.S. PATENT DOCUMENTS 6,214,865 B1    4/2001   Littlefield et al.

FOREIGN PATENT DOCUMENTS

| WO | 2005118565 A1 | 12/2005 |
| WO | 2009124237 A1 | 10/2009 |
| WO | 2013097042 A1 | 7/2013 |
| WO | 2013142999 A1 | 10/2013 |
| WO | 2015000070 A1 | 1/2015 |

OTHER PUBLICATIONS

Berge et al, Pharmaceutical Salts, Journal of Pharmaceutical of Science, Jan. 1977, 66 (No. 1), p. 1-19. (Year: 1977).*
Roberts et al, Modern Experimental Organic Chemistry, 1979, 3rd ed., p. 49-51. (Year: 1979).*
Patent Cooperation Treaty Search Report and Written Opinion for PCT/CA2015/050168, dated May 14, 2015, 14 pages.
Rudolph, Alena, et al., Early introduction of the amino group to the C27-C35 building block of Eribulin, Tetrahedron Letters, vol. 54, Dec. 18, 2013, pp. 7059-7061.
Dong, Cheng-Guo, et al., New synthesis of E7389 C14-C35 and halichondrin C14-C38 building blocks: Reductive cyclization and oxy-michael cyclization approaches, Journal of the American Chemical Society, Jul. 20, 2009, pp. 15642-15646.
Zheng, Wanjun, et al., Macrocyclic ketone analogues of halichondrin B, Bioorganic & Medicinal Chemistry Letters 14, Jul. 30, 2004, pp. 5551-5554.

* cited by examiner

*Primary Examiner* — Taylor V Oh
(74) *Attorney, Agent, or Firm* — Luedeka Neely Group, P.C.

(57) ABSTRACT

Disclosed are salts of a compound of formula 1, as shown below, where $R^1$, $R^2$, $R^3$, $R^{4+}$ $R^5$, $R^6$ and $R^7$ are as described herein. Also, disclosed is a process for the preparation of the salts of the compounds of formula 1, and intermediates used therein. The salts of the compound of formula 1 can be useful for preparation of halichondrin analogs such as eribulin.

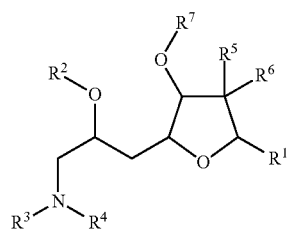

38 Claims, No Drawings

CRYSTALLINE DERIVATIVES OF (S)-1-((2R,3R,4S,5S)-5-ALLYL-3-METHOXY-4-(TOSYLMETHYL)TETRAHYDROFURAN-2-YL)-3-AMINOPROPAN-2-OL

This application is a Section 371 national phase entry of PCT application PCT/CA2015/050168, filed Mar. 6, 2015. This application also claims the benefit of the earlier filing date of U.S. provisional patent application 61/948,875, filed Mar. 6, 2014.

CROSS REFERENCE TO RELATED APPLICATION

This application claims the benefit of and priority to U.S. Provisional Patent Application Ser. No. 61/948,875 filed Mar. 6, 2014 under the title CRYSTALLINE DERIVATIVES OF (S)-1-((2R,3R,4S,5S)-5-ALLYL-3-METHOXY-4-(TOSYLMETHYL)TETRAHYDROFURAN-2-YL)-3-AMINOPROPAN-2-OL. The content of the above patent application is hereby expressly incorporated by reference into the detailed description hereof.

FIELD

The specification relates to crystalline salts of formula 1', as disclosed herein, process for their preparation and their use.

BACKGROUND

Halinchondrin analogs have been disclosed as having anticancer and antimitotic activity (U.S. Pat. No. 6,214,865, incorporated herein by reference). In particular, Halichondrin B has been reported as a potent anticancer agent that was first isolated from the marine sponge *Halichondria okadai* (U.S. Pat. No. 6,214,865; WO 2005/118565 A1 and WO 2009/124237 A1, all incorporated herein by reference). In addition, Eribulin, a Halichondrin B analog, has been reported as having potent anticancer properties (WO 2009/124237 A1, incorporated herein by reference).

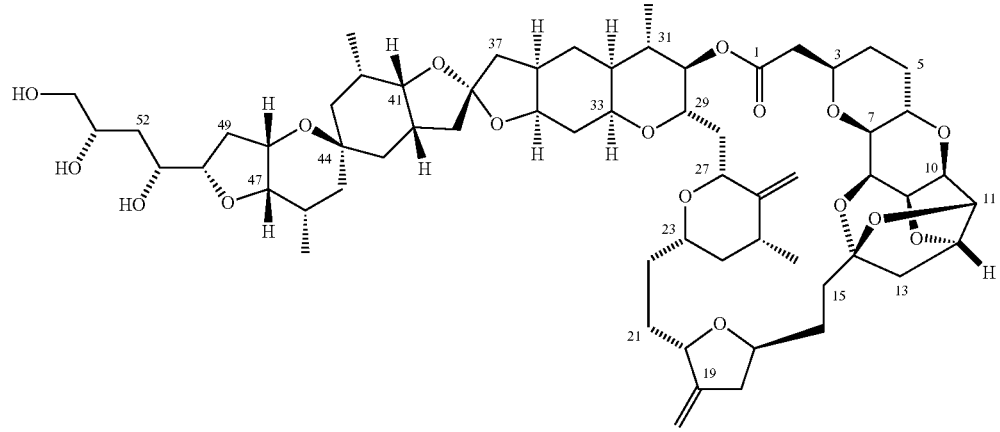

Halichondrin B

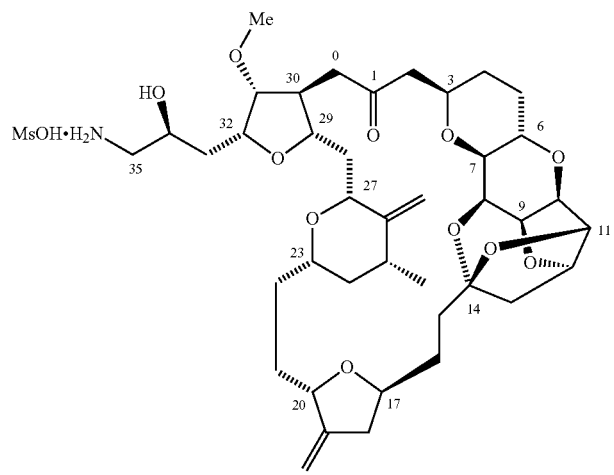

Eribulin mesylate (where Ms = $CH_3SO_2$—)

The synthetic approach described (U.S. Pat. No. 6,214,865; WO 2009/124237 A1, *Bioorg. Med. Chem. Lett.*, 2004, 14, 5551 and *J. Am. Chem. Soc.* 2009, 131, 15642, all incorporated herein by reference) involves introduction of nitrogen in the C27-C35 fragment of eribulin after assembly of the macrocycle. Such an approach can add synthetic steps to the later stages of the synthesis, after the building blocks corresponding to the C1-C13 and C14-C26 fragments have been introduced. The synthesis of those fragments is long and complex; and every additional step in the synthesis can imply an increase in manufacturing costs. In addition, due to the cytotoxic nature of eribulin, late introduction of the nitrogen results in a greater number of steps that can require special safety containment, which can limit throughput and can also increase the cost of producing the active pharmaceutical ingredient (API).

PCT publication numbers WO 2013/097042 and WO 2013/142999 (incorporated herein by reference) disclose process for preparation of the compound of formula 1, which corresponds to the C27-C35 fragment eribulin. The compound of formula 1 can help to mitigate a number of concerns associated with the manufacture of eribulin.

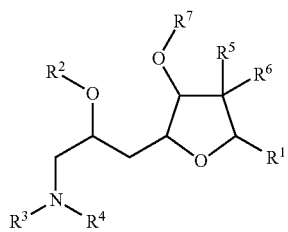

1

In the manufacture of eribulin, a number of the intermediates produced and used during the synthesis of eribulin can be present as liquid, making handling and storage challenging. Moreover, such liquid intermediates can require chromatographic purification that can make handling challenging and manufacturing at an industrial scale inefficient, expensive and undesirable.

There is a need in the art for solid intermediates that can be used in process for preparation of Halichondrin and its analogs, including eribulin. In addition, there is a need in the art for solid intermediates that can be purified by recrystallization, and are solid compounds under ambient conditions, which can assist in handling of such compounds or can help improve manufacturing efficiency. Moreover, there is a need in the art for a process for preparation of such intermediates.

SUMMARY OF THE INVENTION

In one aspect, the specification discloses a salt of formula 1'

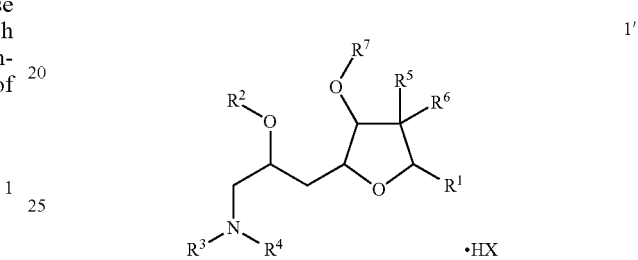

wherein $R^1$, $R^2$, $R^3$, $R^4$, $R^5$, $R^6$, $R^7$ and X are as described herein.

In another aspect, the specification discloses a process for preparation of the salt as disclosed herein.

In a further aspect, the specification discloses a process for recrystallization of the salt as disclosed herein.

In a still further aspect, the specification discloses a process for preparation of a halichondrin analog, including eribulin, the process containing use of the salt as disclosed herein or the process as disclosed herein.

DESCRIPTION OF EXAMPLE EMBODIMENTS

As described above, in one aspect the specification discloses a salt of formula 1'

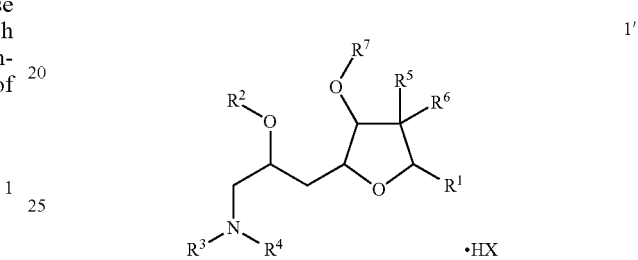

$R^1$ is —$CH_2$—CH=$CR^8R^{8'}$, —$CH_2$—C(=O)—$R^9$ or —$CH_2$—$CH_2$—O—$R^{10}$, wherein
 $R^8$ and $R^{8'}$ each independently is H or a hydrocarbon, the hydrocarbon optionally having one or more heteroatoms;
 $R^9$ $OR^{11}$, wherein $R^{11}$ is H or a hydrocarbon, the hydrocarbon optionally having one or more heteroatoms;
 $R^{10}$ is H or an alcohol protecting group;
$R^2$ is H or an alcohol protecting group;
$R^3$ and $R^4$ each independently is H, allyl, benzyl or substituted benzyl;
or $R^2$ and one of $R^3$ and $R^4$ together form —C($R^{12}$)($R^{13}$)— and the other $R^3$ and $R^4$ is H, allyl, benzyl or a substituted benzyl group, wherein $R^{12}$ and $R^{13}$ each independently is H or a hydrocarbon, the hydrocarbon optionally having one or more heteroatoms;
one of $R^5$ and $R^6$ is H and the other is —$CH_2OR^{14}$ or —$CH_2SO_2$—Ar, or $R^5$ and $R^6$ taken together form =CH—$SO_2$—Ar, wherein
 $R^{14}$ is H or an alcohol protecting group; and
 Ar is an aryl group; and
$R^7$ is H, $C_{1-3}$ alkyl or $C_{1-3}$ haloalkyl; and
HX is an acid.

In one embodiment, the salt has the stereochemical configuration as shown in formula 1a'

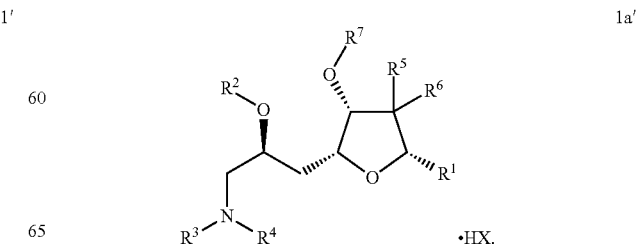

As used herein, salt refers to an ionic compound that can result from the neutralization reaction of an acid and a base. The compound of formula 1 disclosed herein acts as base, by donating a pair of electrons from the nitrogen substituent present in the molecule to a proton from an acid.

An acid as used herein relates to a substance which can act as a proton donor, and aqueous solutions of acids have a pH of less than 7. Examples of proton-donating acids include, for example and without limitation, hydrochloric acid, sulfuric acid, citric acid, hydrobromic acid, hydroiodic acid, nitric acid, phosphoric acid, isonicotinic acid, acetic acid, lactic acid, salicic acid, tartaric acid, O,O'-Di-acyl-tartaric acid, pantotenic acid, ascorbic acid, succinic acid, maleic acid, fumaric acid, gluconic acid, saccharinic acid, formic acid, benzoic acid, glutamic acid, methanesulfonic acid (also referred to as mesylic acid), ethanesulfonic acid, benzenesulfonic acid, p-toluenesulfonic acid, or a pamoic acid.

Using an acid noted above, salt of formula 1' can be formed, and where the salt is a hydrochloric acid salt, sulfuric acid salt, citrate salt, hydrobromic acid salt, hydroiodic acid salt, nitric acid salt, bisulfate salt, phosphoric acid salt, isonicotinic acid salt, acetic acid salt, lactic acid salt, salicic acid salt, tartaric acid salt, O,O'-Di-acyl-tartaric acid, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt (also referred to as mesylic acid salt), ethanesulfonic acid salt, benzenesulfonic acid salt, p-toluenesulfonic acid salt, or a pamoic acid salt (pamoate).

The term "hydrocarbon", as used herein, refers to a group that contains hydrogen and carbon, linked generally via a carbon backbone, but may optionally include heteroatoms. Thus, groups like methyl, ethoxyethyl, 2-pyridyl, and trifluoromethyl are considered to be hydrocarbyl for the purposes of this application. Hydrocarbyl groups include, but are not limited to aryl, heteroaryl, carbocycle, heterocycle, alkyl, alkenyl, alkynyl, and combinations thereof.

The term "heteroatom" as used herein means an atom of any element other than carbon or hydrogen. Preferred heteroatoms are nitrogen, oxygen, silicon and sulfur.

The term "alcohol protecting group" as used herein is not particularly limited, and should be known to a skilled worker or can be determined (see, for example, Wuts, P. G. M.; Greene, T. W. *Greene's Protective Groups in Organic Synthesis*, 4th ed.; John Wiley & Sons, Inc.: Hoboken, N.J., 2007). In one embodiment, for example and without limitation, the protecting group forms an ester, ether or is a silyl-protecting group. In a further embodiment, for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS), tri-iso-propyl-silyloxymethyl (TOM), or triisopropylsilyl (TIPS).

In another embodiment, for example and without limitation, the alcohol protecting group is an acid-stable alcohol protecting group (see, for example, Wuts, P. G. M.; Greene, T. W. *Greene's Protective Groups in Organic Synthesis*, 4th ed.; John Wiley & Sons, Inc.: Hoboken, N.J., 2007, incorporated herein by reference). An acid-stable protecting group as used herein refers to a protecting group that can resist cleavage from the molecule (and lead to deprotection) under acidic conditions used for formation of the salt of formula 1'. The acid-stable alcohol protecting groups are not particularly limited, and can depend upon the conditions used for formation of the salt of formula 1'. In one embodiment, for example and without limitation, the acid-stable alcohol protecting is tert-butyl ether, allyl ether, benzyl ether, p-methoxybenzyloxymethyl ether (PMBM), [(3,4-dimethoxybenzyl)oxy]methyl ether (DMBM) [$(CH_3O)_2C_6H_3CH_2OCH_2O$—], tert-butoxymethyl ether, 2-(trimethylsilyl)ethoxymethyl ether (SEM), 1,1,1,3,3,3-hexafluoro-2-phenylisopropyl ether (HIP), 2-trimethylsilylethyl ether, prenyl ether, p-methoxyphenyl ether, p-methoxybenzyl ether (PMB), tert-butyldiphenylsilyl ether (TBDPS), tribenzylsilyl, benzoate, or acetate.

The term "silyl group" as used herein is not particularly limited, and should be known to a person of skill in the art. In one embodiment, for example and without limitation, the silyl group refers to the general formula "$R_3Si$—", where R is a hydrocarbon; and can include the silyl protecting groups noted above. In a further embodiment, for example and without limitation, the silyl group can optionally have one or more heteroatoms.

The term "acyl group" as used herein is not particularly limited, and should be known to a person of skill in the art. In one embodiment, for example and without limitation, the acyl group refers to the general formula "$RC(=O)$—", where R is a hydrocarbon; and can also include the acyl protecting groups noted above.

The term "sulfonyl group" as used herein is not particularly limited, and should be known to a person of skill in the art. In one embodiment, for example and without limitation, the sulfonyl group refers to the general formula "$RSO_2$—", where R is a hydrocarbon. In a further embodiment, for example and without limitation, the sulfonyl group can optionally have one or more heteroatoms.

The term "alkoxycarbonyl group" as used herein is not particularly limited, and should be known to a person of skill in the art. In one embodiment, for example and without limitation, the alkoxycarbonyl group refers to the general formula "$R$—$O$—$C(=O)$—", where R is a hydrocarbon.

The term "alkyl" as used herein is not particularly limited and should be known to a person of skill in the art; and refers to substituted or unsubstituted saturated hydrocarbon groups, including straight-chain alkyl and branched-chain alkyl groups, including haloalkyl groups such as trifluoromethyl and 2,2,2-trifluoroethyl, etc. In one embodiment, for example and without limitation, the alkyl group is a $C_{1-6}$ alkyl.

The term $C_{1-6}$alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1,2-dimethylbutyl, 1-ethyl-2-methylpropyl, 1,1,2-trimethylpropyl, 1,1-dimethylbutyl, 2,2-dimethylbutyl, 2-ethylbutyl, 1,3-dimethylbutyl, 2-methylpentyl or 3-methylpentyl.

The term "aryl" as used herein is not particularly limited, and should be known to a person of skill in the art. In one embodiment, for example and without limitation, the aryl group is a $C_{6-14}$ aryl. In another embodiment, for example and without limitation, aryl includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Examples of aryl include benzene, naphthalene, phenanthrene, phenol, aniline, anthracene, and phenanthrene.

The salt of formula 1' can be formed dissolving the compound of formula 1 in an organic solvent, followed by addition of a proton-donating acid to the organic solvent to protonate the compound of formula 1 and form the salt.

The organic solvent used for dissolving the compound of formula 1 is not particularly limited and can include, for example and without limitation, ethyl acetate, isopropyl acetate, ethyl acetate, tetrahydrofuran (THF), dichloromethane (DCM), dimethylformamide (DMF), acetonitrile, propylene carbonate, n-butanol, isopropanol (IPA), n-propanol, ethanol, methanol, toluene, 1,4-dioxane, chloroform, methyl tert-butyl ether (MTBE) or diethyl ether, or a combination thereof.

The addition of the acid can take place at room temperature, although the temperature for addition is not particularly limited. Moreover, addition of the acid can be carried out with agitation of the solution, or agitation can performed after addition of the acid. In one embodiment, for example and without limitation, the acid is added with agitation, and the solution is agitated from about 2 to about 48 hours, and all values in between, such as, 3, 4, 5, 10, 15, 20 or 24 hours.

Once the salt forms, it can be separated from the solvent. The method of separation is not particularly limited, and can include, for example and without limitation, filtration. The crude salt can be purified by recrystallization to obtain a salt having higher level of purity.

Recrystallization as used herein refers to a technique used to purify the salt, and should be understood by a person of skill in the art. By dissolving both impurities and the salt in an appropriate solvent, the desired salt can be coaxed out of solution, leaving the impurities behind in solution. The process can be carried out by dissolving the salt, as disclosed herein, in a second organic solvent. The second organic solvent can be chosen from the list of organic solvents listed above. The dissolution is carried out at elevated temperatures, such as being above room temperature, using a minimal amount of solvent that is required for dissolution of the salt. Upon dissolution, the solution is allowed to cool and permit crystallization of the salt out of the solution.

The conditions for recrystallization are not particularly limited. In one embodiment, for example and without limitation, the organic solvent used for recrystallization is a polar aprotic solvent or a polar protic solvent. The solvent used for recrystallization can include solvents described herein above. In a particular embodiment, for example and without limitation, the solvent used is acetonitrile.

To dissolve the salt in the solvent, the solvent can be heated to its boiling point or at elevated temperatures, such as, from about 50° C. to about 150° C.±10° C., and all values in between. Once the salt dissolves, the solution is allowed to return to room temperature to allow crystallization of the salt. In one embodiment, the solution can be further cooled to assist in increasing the amount of salt recrystallized. For instance, the solution can be cooled to from about −10° to 10° C., and all values in between. Once the salts have recrystallized, the purified salt can be separated from the solvent by separation methods, such as, for example and without limitation, filtration.

The compound of formula 1 as described above can be prepared using a process containing the step of:
converting the terminal alcohol of the compound of formula 2 into an amine to form the compound of formula 1a

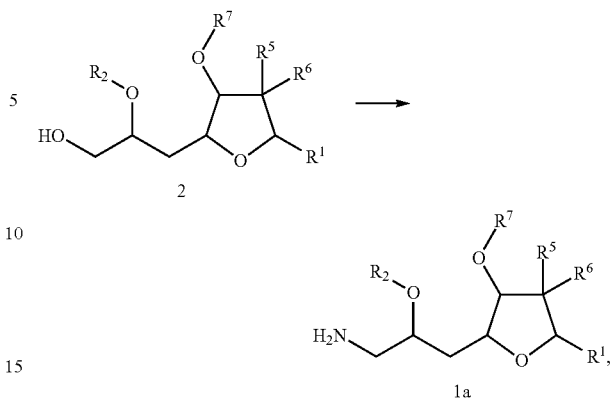

wherein $R^1$, $R^2$, $R^3$, $R^4$, $R^5$, $R^6$ and $R^7$ are as described above.

The process for conversion of the alcohol group into an amine group is not particularly limited. In one embodiment, for example and without limitation, the conversion is carried out by converting the alcohol into a leaving group to form an intermediate, followed by substitution of the leaving group by an amine or other nitrogen based nucleophile to form the compound of formula 1.

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is mesylate or tosylate.

The amine or other nitrogen based nucleophile used for formation of the amine is not particularly limited. In one embodiment, for example and without limitation, the amine used for the substitution reaction is ammonia. In another embodiment, for example and without limitation, the nitrogen based nucleophile is an azide. The azide used is also not particularly limited, and can be, in one embodiment for example, trimethylsilyl azide ($TMSN_3$).

The organic solvent used in the reactions described herein is not particularly limited and should be known to a person of skill in the art or can be determined. The particular solvent used would depend upon the reactants and the reaction being carried out, to allow the reaction to proceed. In one embodiment, for example and without limitation, the amination is carried out using ammonia, with methanol being used as a solvent.

In one embodiment, in the compound of formula 1a formed after amination and where $R^2$ is H, the hydroxyl and amine functional groups of the compound are protected. Alcohol protecting group, as described above, can be used to protect the alcohol group, and where $R^2$ is as described above.

The amine protecting group as used herein is not particularly limited and should be known to a person of skill in the art (see, for example, Wuts, P. G. M.; Greene, T. W. *Greene's Protective Groups in Organic Synthesis*, 4th ed.; John Wiley & Sons, Inc.: Hoboken, N.J., 2007, incorporated herein by reference). In one embodiment, for example and without limitation, amine protecting group can include p-methoxybenzyl (PMB), 3,4-Dimethoxybenzyl (DMPM) or p-methoxyphenyl (PMP). In a further embodiment, the amine is unprotected.

In one embodiment, for example, in the compound of formula 1, $R^1$ is —$CH_2$—CH=$CH_2$. In another embodiment, for example, in the compound of formula 1 $R^1$ is —$CH_2$—C(=O)$R^9$, where $R^9$ is as disclosed herein. The process for formation of the compound of formula 1 where $R^1$ is —$CH_2$—C(=O)$R^9$ is not particularly limited. In one embodiment, the compound of formula 1 where $R^1$ is —$CH_2$—C(=O) $R^9$ is formed from a compound where $R^1$ is —$CH_2$—CH=$CH_2$. The process for conversion is not particularly limited. In one embodiment, for example and without limitation, the conversion is carried out by oxidatively cleaving the alkene to form a carboxylic acid. The carboxylic acid, optionally, can subsequently be converted into an ester using reagents and chemical steps that should be known to a person of ordinary skill in the art.

The process for oxidatively cleaving the alkene to a carboxylic acid is not particularly limited and should be known to a person of skill in the art or can be determined. In one embodiment, for example and without limitation, the oxidative cleavage is performed using osmium tetroxide, potassium permanganate, sodium periodate or by ozonolysis.

In one embodiment in the compound of formula 1, $R^5$ and $R^6$ each independently is H, —$CH_2OR^{14}$ or —$CH_2SO_2$—Ar, or $R^5$ and $R^6$ taken together form =CH—$SO_2$—Ar, where Ar is aryl and $R^{14}$ is H or an alcohol protecting group. In a further embodiment in the compound of formula 1, one of $R^5$ and $R^6$ is —$CH_2SO_2$-Ph. In a still further embodiment, for example, the one of $R^5$ and $R^6$ is —$CH_2SO_2$-Ph and the carbon to which it is attached has the S-configuration.

The process for formation of a compound of formula 1 where $R^5$ and $R^6$ is, as described above, not particularly limited. In one embodiment, for example a compound of formula 3 is converted into the compound of formula 1, where one of $R^5$ and $R^6$ is —$CH_2SO_2$-Ph.

The process for conversion of the alcohol group into $R^5$ and $R^6$ as described above in the compound of formula 1 is not particularly limited. In one embodiment, for example and without limitation, the alcohol is oxidized to a ketone ("R'—C(=O)—R") prior to conversion to the compound of formula 1. The oxidation of the alcohol is not particularly limited, and should be known to a skilled worker or can be determined. In one embodiment, for example and without limitation, the oxidation is performed using a chromium-based reagent, such as Collins reagent, pyridinium dichromate (PDC) or pyridinium chlorochromate (PCC); activated dimethyl sulfoxide (DMSO), such as, Swern oxidation, Moffatt oxidation or Doering oxidation; or hypervalent iodine compounds, such as, Dess-Martin periodinane or 2-iodoxybenzoic acid.

Following oxidation of the alcohol to a ketone, the ketone functional group can be, in one embodiment, for example and without limitation, converted into an alkene. The reaction to convert a ketone to an alkene is not particularly limited, and should be known to a skilled worker or can be determined. In one embodiment, for example and without limitation, the ketone can be converted into an alkene using the Peterson olefination, the Wittig reaction or the like. In a further embodiment, for example and without limitation, the ketone is converted into an alkene using $(EtO)_2$POCH$_2$SO$_2$Tol, with Tol being tolyl (4-MeC$_6$H$_4$—).

Upon formation of the alkene, the compound can be reduced to alkane using a reducing agent. The reducing agent used is not particularly limited and can be determined by a skilled worker. In one embodiment, for example and without limitation, the reduction is carried out using a hydride source. The hydride source used is not particularly limited and should be known to a skilled worker or can be determined. In one embodiment, for example and without limitation, the hydride source is Stryker's Reagent ([(PPh$_3$)CuH]$_6$) or sodium borohydride triacetate (NaBH(OAc)$_3$).

In one embodiment in the compound of formula 1, $R^7$ is H, $C_{1-3}$ alkyl or $C_{1-3}$ haloalkyl. In a further embodiment, for example and without limitation, $R^7$ is $C_{1-3}$ alkyl. In a still further embodiment, for example and without limitation, $R^7$ is methyl.

The process for preparation of compounds of formula 1 will now be described with reference to Scheme 1, shown below.

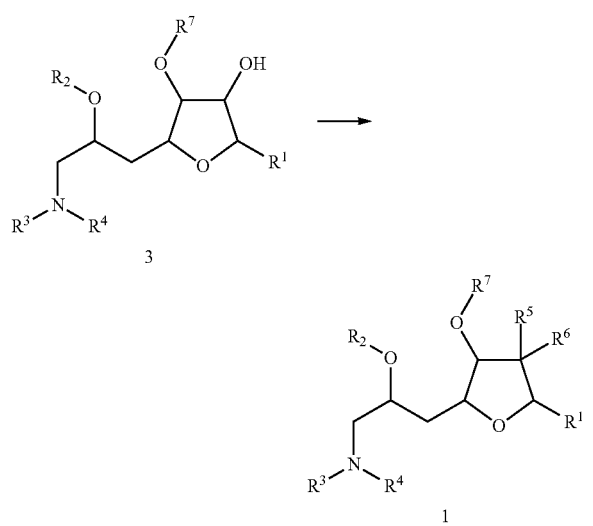

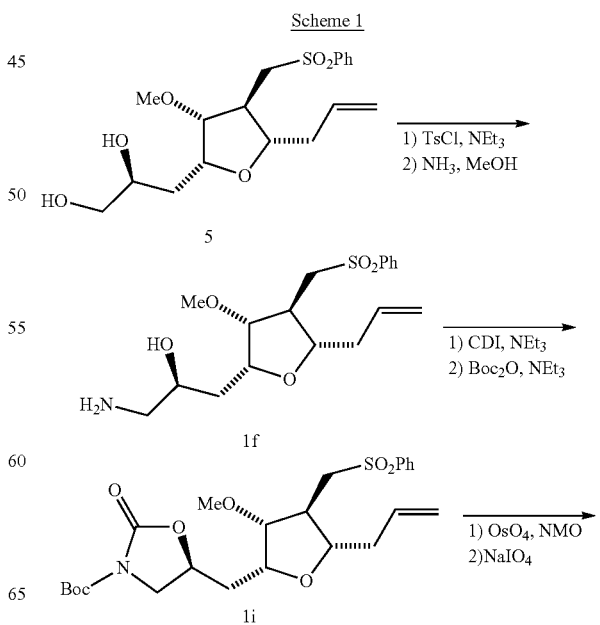

Scheme 1

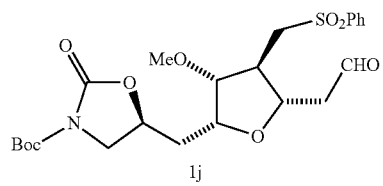

The compound of formula 5, as shown in Scheme 1, can be obtained from D-(+)-Glucurono-6,3-lactone according to the conditions as described in *Pure Appl. Chem.* 2003, 75, 1-17, incorporated herein by reference. The terminal alcohol in the compound of formula 5 can be converted into a leaving group, such as a tosylate, followed by nucleophillic substitution with an amine, such as ammonia, that leads to formation of the compound of formula 1f. Reaction with 1,1'-carbonyldiimidazole (CDI) and protection of the oxazolidinone with di-tert-butyl pyrocarbonate ($Boc_2O$) leads to the compound of formula 1i. The alkene in the compound of formula 1i can then be converted to an aldehyde of formula 1j, by oxidation using osmium tetroxide and N-methyl morpholine N-oxide, followed by reaction with sodium periodate ($NaIO_4$).

EXAMPLES

The invention is now described by way of examples, which disclose embodiments of the inventions, and are not intended to be limiting of the invention as described and set herein.

Example 1

Preparation of Compound of Formula 5a

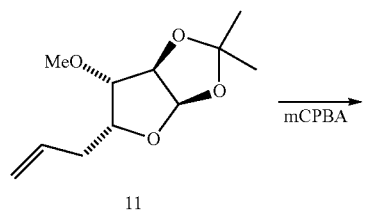

Epoxide of formula 5a was prepared by oxidation of compound of formula 11 with m-Chloroperbenzoic acid (m-CPBA), following the procedure described in *Org. Lett.* 2010, 12, 744.

Example 2

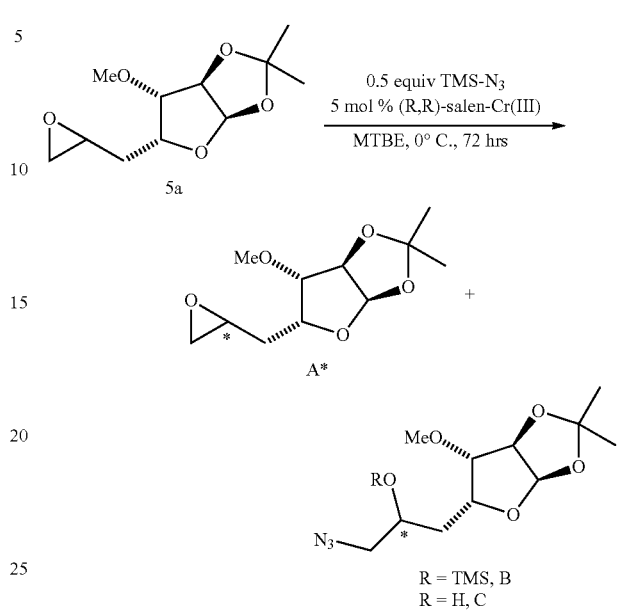

A dry reaction vessel equipped with a stir bar and rubber septum, under an atmosphere of $N_2$, was charged with compound 5a (1 wt. parts). Compound 5a was dissolved in anhydrous methyl t-butyl ether (MTBE, 1.6 vol. parts) and the resulting solution was cooled to 0° C. (R,R)-salen-Cr(III) (0.01 eq, 0.03 wt. parts) and trimethylsilyl azide ($TMSN_3$) (0.50 eq, 0.25 wt. parts) were added to the solution of 5a at 0° C. and the resulting reaction mixture was stirred at 0° C. for 72 hrs. The volatiles were removed under reduced pressure and the crude mixture was separated by column chromatography (stationary phase: $SiO_2$, eluent: 1:0-7:13 heptanes:EtOAc) to afford single isomers A* (0.49 eq.) and B+C (0.49 eq.) as colourless oils.

Example 3

Preparation of Compound of Formula 2a

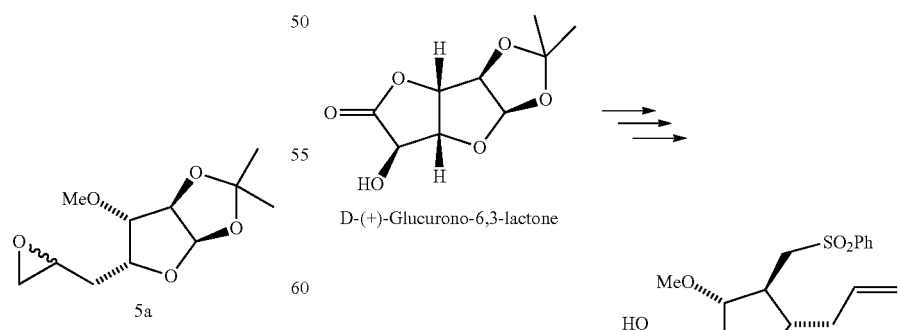

The diol of formula 2a was prepared from D-(+)-Glucurono-6,3-lactone according to the conditions described in *Pure Appl. Chem.* 2003, 75, 1-17.

Example 4

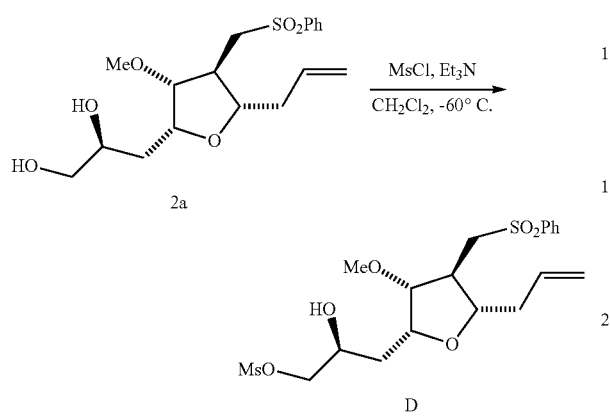

Compound 2a (1 wt. parts) is dissolved in CH$_2$Cl$_2$ (14 vol. parts) and the resulting solution is cooled to an internal temperature of −60° C. Triethylamine (Et$_3$N) (1.1 eq., 0.3 wt. parts) and methanesulfonyl chloride (MsCl) (1.1 eq., 0.3 wt. parts) are added sequentially at −60° C. The internal temperature of the reaction mixture is kept below −52° C. The reaction is run at −60° C. for 45 min, until no further conversion is detected by thin layer chromatography (TLC) (1:1 heptanes:EtOAc). The reaction is quenched with water (5 vol. parts), warmed to room temperature and the organic layer is separated. The aqueous layer is further extracted with CH$_2$Cl$_2$ (2×5 vol. parts) and the combined organic layers are dried over Na$_2$SO$_4$, filtered and concentrated in vacuo. The crude mixture is purified by column chromatography (stationary phase: SiO$_2$, 1:0-1:1 heptanes:EtOAc) to afford compound of formula D.

Example 5

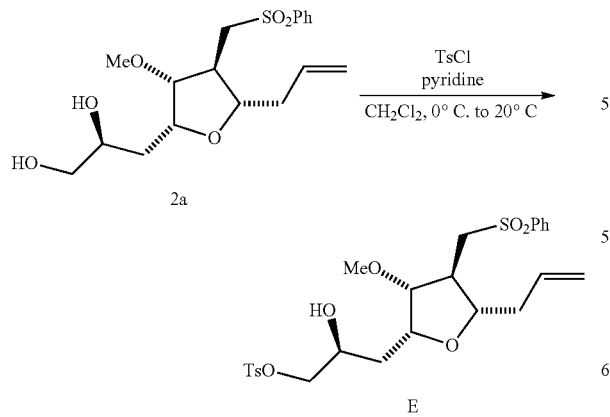

Compound 2a (1 wt. parts) is dissolved in CH$_2$Cl$_2$ (5.7 vol. parts) and the resulting solution is cooled to 0° C. To the solution of 2a is added pyridine (5.0 eq., 1.1 wt. parts), catalytic 4-dimethylaminopyridine (DMAP) and 4-toluenesulfonyl chloride (TsCl) at 0° C. The reaction mixture is allowed to slowly warm to room temperature and is stirred at room temperature until TLC analysis (eluent: 1:1 heptanes:EtOAc) indicates the reaction to be complete. The reaction is quenched with saturated aqueous NH$_4$Cl (5 vol. parts). The organic layer is separated and washed once more with saturated aqueous NH$_4$Cl, followed by 1M aqueous HCl. The organic layer is dried over Na$_2$SO$_4$, filtered and concentrated in vacuo. The crude product is purified by column chromatography (stationary phase: SiO$_2$, eluent: 3:1-1:1 heptanes:EtOAc) to obtain E.

Example 6

Preparation of Compound of Formula 1e

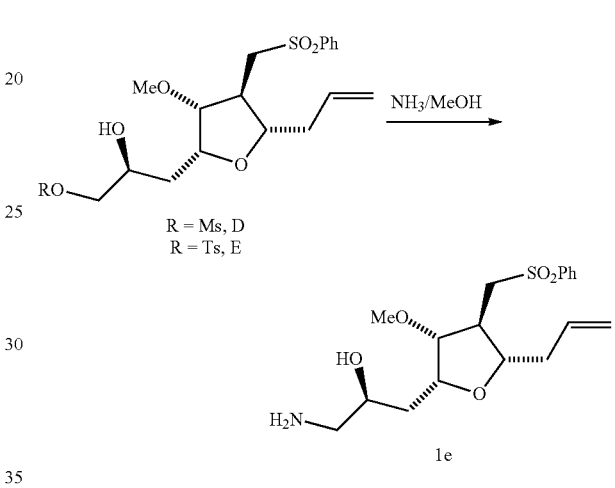

Compound D or E (1 wt. parts). is dissolved in 7 N NH$_3$ in methanol (33 vol. parts) and stirred at room temperature for 3 days, or until TLC analysis (eluent: 1:1 heptanes: EtOAc) indicates that the starting material is consumed. The volatiles are removed under reduced pressure and the crude mixture is redissolved in CH$_2$Cl$_2$ and washed with saturated aqueous NaHCO$_3$. The organic layer is separated, dried over Na$_2$SO$_4$, filtered and concentrated under reduced pressure to afford crude 1e which is used without further purification.

Example 7

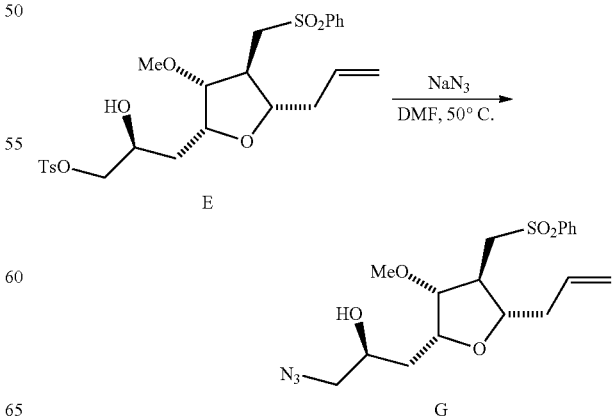

Compound E (1 wt. parts) is dissolved in dimethylformamide (DMF) (20 vol. parts) and to this solution is added NaN₃ (6.5 eq. 0.82 wt. parts) at room temperature. The reaction mixture is heated to 50° C. until TLC analysis (eluent: 1:1 heptanes:EtOAc) indicates the starting material to be consumed. The reaction mixture is quenched with water, diluted with diethyl ether and the layers are separated. The aqueous layer is further extracted with diethyl ether and the combined organics are dried over Na₂SO₄, filtered and concentrated under reduced pressure. The crude product G is used without further purification.

Example 8

Preparation of the Compound of Formula 1f

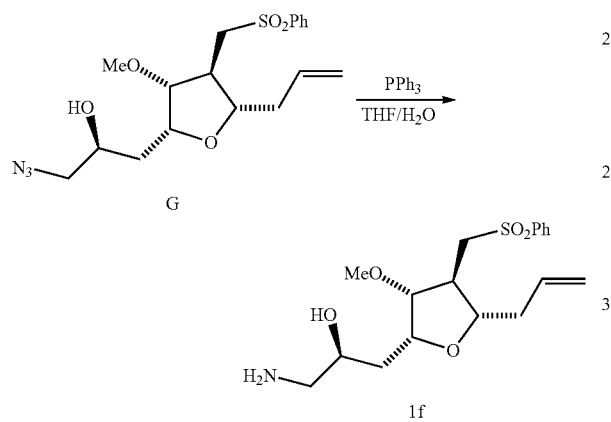

Crude product G (1 wt. parts) is dissolved in tetrahydrofuran (THF) (10 vol. parts) and to this solution is added triphenylphosphine (PPh₃) (1.1 eq. 0.58 wt. parts) and water (1 vol. parts). The reaction mixture is stirred at room temperature until TLC analysis (eluent: 1:1 heptanes:EtOAc) indicates that the starting material has been consumed. The reaction is quenched with water and diluted with ethyl acetate (EtOAc). The layers are separated and the aqueous layer is extracted twice more with EtOAc. The combined organics are dried over Na₂SO₄, filtered and concentrated to afford crude 1f, which is used without purification.

Example 9

Preparation of Compound of Formula 1g

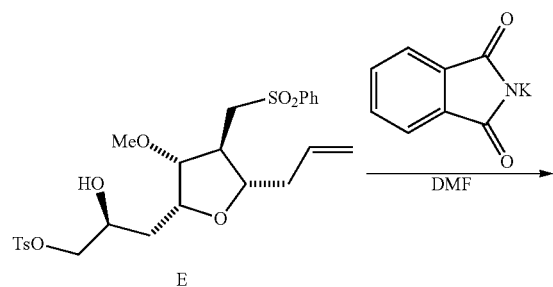

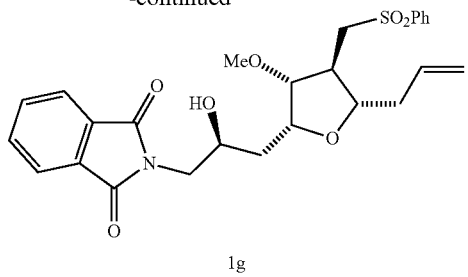

Compound E (1 wt. parts) is dissolved in dimethylformamide (DMF) (20 vol. parts) and to this solution is added potassium phthalimide (3.0 eq. 1.1 wt. parts) at room temperature. The reaction mixture is stirred at room temperature until TLC analysis (eluent: 1:1 heptanes:EtOAc) indicates that the starting material is consumed. The reaction mixture is quenched with water, diluted with diethyl ether and the layers are separated. The aqueous layer is further extracted with diethyl ether and the combined organics are dried over Na₂SO₄, filtered and concentrated under reduced pressure. The crude product is purified by column chromatography (stationary phase: SiO₂, eluent: 1:0-1:1 heptanes:EtOAc) to afford 1g.

Example 10

Preparation of Compound of Formula 1h

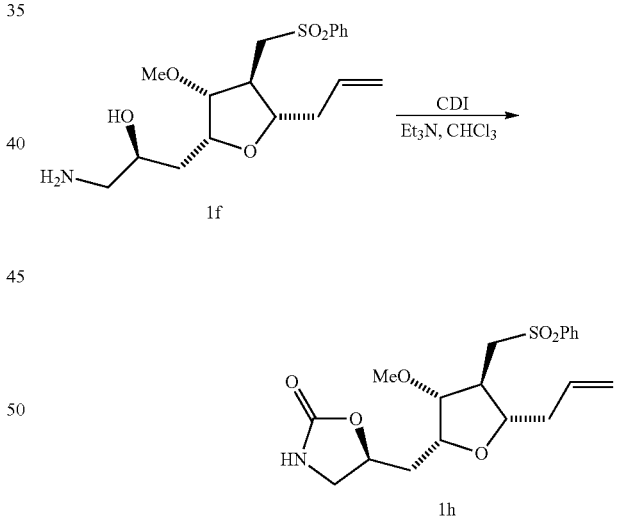

Compound 1f (1 wt.) is dissolved in CHCl₃ (11 vol. parts) and to the resulting solution triethylamine (Et₃N) (1.5 eq., 0.42 wt. parts) and 1,1'-carbonyldiimidazole (CDI) (1.5 eq., 0.33 wt. parts) are added. The reaction mixture is stirred at room temperature until TLC analysis (eluent: 95:5 CH₂Cl₂:MeOH) shows that the starting material has been consumed. The reaction mixture is diluted with CH₂Cl₂ and washed twice with water and once with brine. The organic layer is dried over Na₂SO₄, filtered and concentrated. The crude product is purified by column chromatography (stationary phase: SiO₂, eluent: 9:1-6:4 CH₂Cl₂:acetone) to afford 1h.

Example 11

Preparation of Compound of Formula 1i

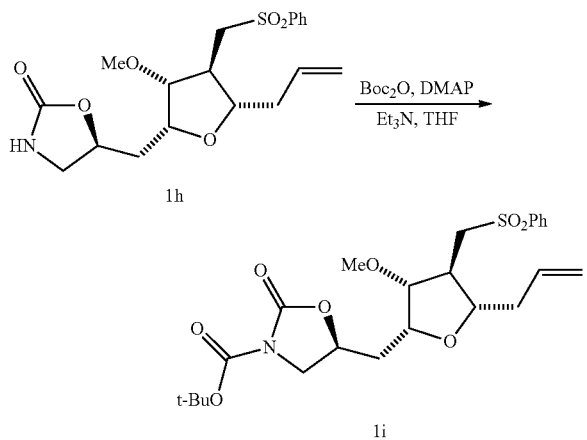

Compound 1h (1 wt. parts) is dissolved in tetrahydrofuran (THF) (7.1 vol. pars) and to this solution are added triethylamine ($Et_3N$) (1.2 eq, 0.29 wt. parts), catalytic 4-dimethylaminopyridine (DMAP) and di-tert-butyl pyrocarbonate ($Boc_2O$) (1.3 eq., 0.71 wt. parts) at room temperature. The reaction is stirred at room temperature until TLC analysis (eluent: 8:2 $CH_2Cl_2$:acetone) shows that the starting material has been consumed. The reaction mixture is diluted with ethyl acetate (EtOAc) and washed sequentially with water and 1M aqueous HCl. The organic layer is dried over $Na_2SO_4$, filtered and concentrated to afford crude 1i, which is used without further purification.

Example 12

Preparation of Compound 1j

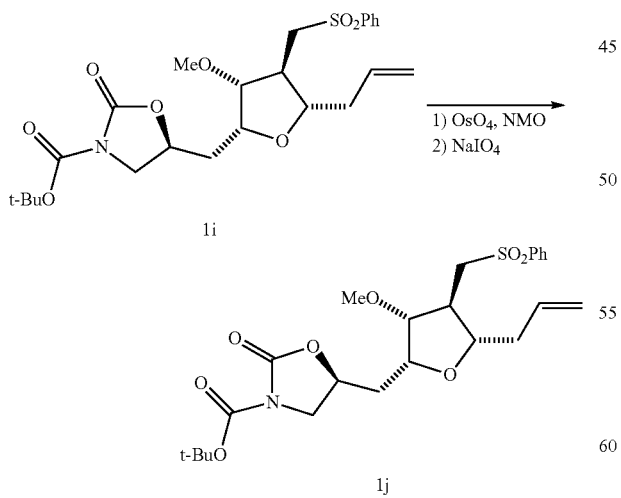

To a solution of alkene 1i (1.28 mmol) in $CH_2Cl_2$ (8 mL) at room temperature is added 4-methylmorpholine N-oxide (NMO) (3.84 mmol, 3.0 equiv) and a solution of $OsO_4$ (0.10M in $H_2O$, 0.020 equiv). The resulting mixture is vigorously stirred for 1.5h and 0.5M aqueous solution of sodium bisulfite (10 mL) is then added. After stirring for 30 min at room temperature, the mixture is extracted with $CH_2Cl_2$ (10 mL×3) and the combined organic layers are washed with brine (10 mL), dried over $MgSO_4$, filtered and concentrated under reduced pressure. The resulting residue is dissolved in $CH_2Cl_2$ (10 mL) and a saturated $NaHCO_3$ aqueous solution (0.25 mL) is added, followed by slow addition of $NaIO_4$ (3.84 mmol, 3.0 equiv) with vigorous stirring. After stirring for 5 h at room temperature, the reaction mixture is filtered and the resulting filtrate is concentrated under reduced pressure to give crude compound 1j.

Example 13

Preparation of Compound of Formula 1k

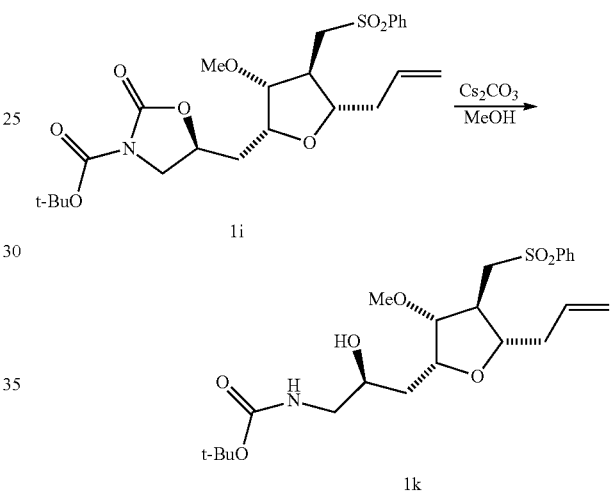

Compound 1i (1 wt. parts) is dissolved in methanol (MeOH) (32 vol. parts) and to this solution is added $Cs_2CO_3$ (0.2 eq, 0.13 wt. parts) at room temperature. The reaction is stirred at room temperature until TLC analysis (eluent: 8:2 $CH_2Cl_2$:acetone) shows that the starting material has been consumed. The reaction mixture is partitioned between water and ethyl acetate (EtOAc) and the organic layer is separated. The aqueous layer is extracted twice more with EtOAc and the combined organics are dried over $Na_2SO_4$, filtered and concentrated under reduced pressure to afford 1k.

Example 14

Preparation of Compound of Formula 1m

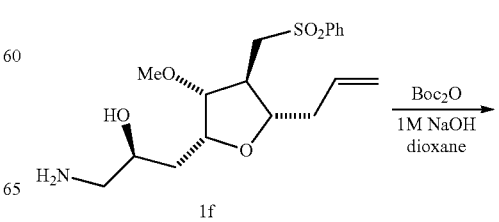

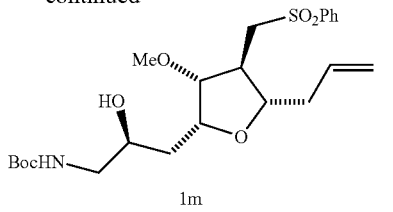

To a solution of 1f (2.3 g, 6.3 mmol, 1.0 eq) in 1M aqueous NaOH (30 mL) and dioxane (30 mL) at room temperature was added a solution of di-tert-butyl dicarbonate (1.6 g, 7.5 mmol, 1.2 eq.) in 1,4-dioxane (30 mL), in one portion. The reaction mixture was stirred at room temperature for 16 hours. TLC showed that the reaction was complete. The reaction was quenched with 1M aqueous HCl until the pH of the reaction mixture reached 6-7. The total volume of the reaction mixture was reduced by half under reduced pressure and subsequently partitioned between ethyl acetate (100 mL) and additional water (100 mL). The layers were separated and the aqueous layer was further extracted with ethyl acetate (2×100 mL) and the combined organic layers were washed with brine (100 mL), dried over MgSO$_4$ and concentrated to a light yellow oil. The crude 1m was used in the subsequent step without any further purification.

Example 15

Preparation of Compound of Formula 1n

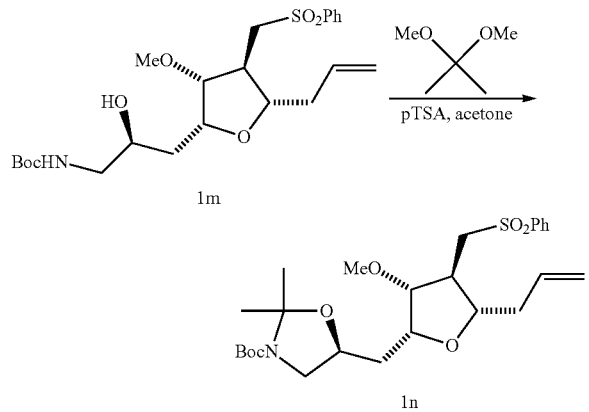

To a solution of crude 1m (6.3 mmol, 1.0 eq.) in acetone (100 mL) was added 2,2-dimethoxypropane (7.7 mL, 63 mmol, 10 eq.) in one portion, followed by p-toluenesulfonic acid (pTSA, 69 mg, 0.6 mmol, 0.1 eq.) at room temperature. The reaction mixture was stirred at room temperature for 16 hrs. TLC (Eluent: heptane/EtOAc 1:1) showed that the reaction was complete as indicated by disappearance of starting material. The reaction was quenched with triethylamine (0.1 mL, 0.7 mmol, 0.11 eq) and the volatiles were removed under reduced pressure. The crude material was dissolved in dichloromethane and purified by column chromatography on silica gel using a gradient 5-10% acetone in dichloromethane as eluent to afford in (yield: 79% over two steps) as a sticky colorless oil.

Example 16

Preparation of Compound of Formula 1o

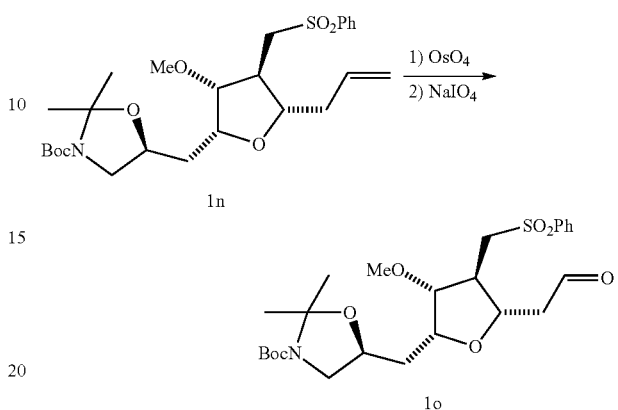

To a solution of 1n (5.5 g, 10.8 mmol, 1.0 eq.) in dichloromethane (60 mL) was added 4-methylmorpholine-N-oxide (3.8 g, 32.4 mmol, 3.0 eq) at room temperature, followed by a solution of OsO$_4$ (2.5% (w/w) in t-BuOH, 1.4 mL, 0.11 mmol, 0.01 eq), dropwise. The reaction mixture was stirred for 2.5 hours and quenched with 10% (w/w) aqueous solution of Na$_2$S$_2$O$_3$ (100 mL). The resulting mixture was stirred for 15 minutes and the layers were separated. The aqueous layer was extracted with additional dichloromethane (2×50 mL) and the combined organics were dried over MgSO$_4$, filtered and concentrated under reduced pressure to afford a diol intermediate, which was used in the subsequent step without any further purification.

In a separate 250 mL round-bottom flask, NaIO$_4$ (6.9 g, 32 mmol, 3.0 eq) was suspended in dichloromethane (20 mL) and saturated aqueous sodium bicarbonate solution (3 mL) was added. The diol intermediate (from the previous step) was dissolved in dichloromethane (40 mL) and added to the reaction mixture at room temperature. The reaction mixture was stirred for 16 hours. The reaction solution was decanted from the reaction vessel, washed with saturated aqueous sodium bicarbonate solution (50 mL), brine (50 mL) and dried over MgSO$_4$, filtered and concentrated under reduced pressure. The product was purified by column chromatography on silica gel using a gradient 5-10% acetone in dichloromethane as eluent, to afford the product 1o as a sticky colourless oil (yield: 83% over 2 steps).

Example 17

Preparation of Compound of Formula 1p

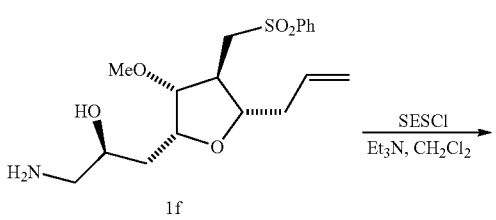

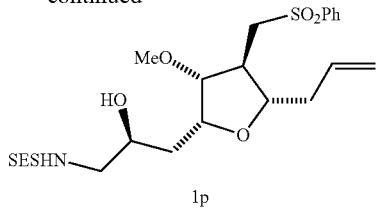

1p

To a solution of the amino alcohol (100 mg, 0.27 mmol, 1.0 eq) in anhydrous dichloromethane (3 mL) at 0° C. was added triethylamine (75 µL, 0.54 mmol, 2.0 eq.) and 2-(trimethylsilyl)ethanesulfonyl chloride (SESCl, 0.1 mL, 0.53 mmol, 1.95 eq.) in one portion. The reaction mixture was stirred at 0° C. for 15 min before the ice bath was removed. The reaction mixture was then warmed to room temperature (20° C.) and stirred for 3 hours. TLC (Eluent: heptane/EtOAc 1:1) showed that the reaction was complete as indicated by disappearance of starting material. The reaction was quenched with saturated aqueous ammonium chloride solution (10 mL), further diluted with dichloromethane (10 mL) and the layers separated. The aqueous layer was further extracted with dichloromethane (2×10 mL) and the combined organic layers were washed with brine (10 mL), dried over MgSO$_4$ and concentrated. The crude product was purified by column chromatography on silica gel using a gradient 10-20% acetone in dichloromethane as eluent to afford the SES-protected amino alcohol 1p (yield: 53%) as a sticky colourless oil.

Example 18

Preparation of Compound of Formula 1q

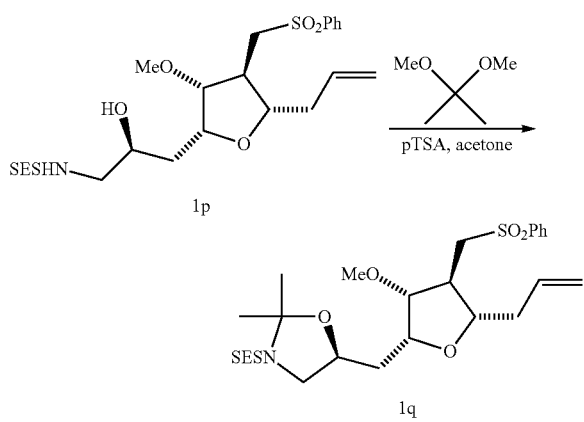

To a solution of the SES-protected amino alcohol 1p (75 mg, 0.14 mmol, 1.0 eq.) in acetone (2.5 mL) was added 2,2-dimethoxypropane (0.17 mL, 1.4 mmol, 10 eq.) in one portion, followed by p-toluenesulfonic acid (3 mg, 0.01 mmol, 0.1 eq.) at room temperature. The reaction mixture was stirred at room temperature for 16 hrs. The reaction was quenched with saturated aqueous sodium bicarbonate solution (10 mL) and further diluted with methyl t-butyl ether (MTBE) (10 mL). The layers were separated and the aqueous layer was further extracted with MTBE (2×10 mL). The combined organic layers were dried over MgSO$_4$, filtered and concentrated under reduced pressure. The crude material was dissolved in dichloromethane and purified by column chromatography on silica gel using a gradient 5-10% acetone in dichloromethane as eluent to afford SES-acetonide protected amino alcohol 1q (yield: 46%) as a colorless oil.

Example 19

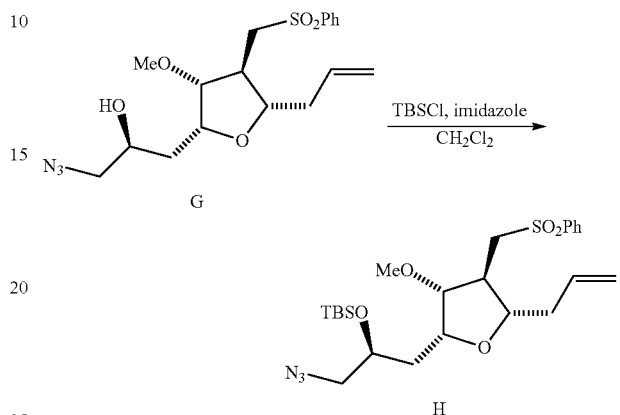

To a solution of the crude azido alcohol G (0.19 mmol, 1.0 eq.) in anhydrous dichloromethane (2 mL) were added imidazole (16 mg, 0.23 mmol, 1.2 eq.), tert-butyldimethylsilyl chloride (TBSCl) (34 mg, 0.23 mmol, 1.2 eq.) and a catalytic amount of DMAP at room temperature. The reaction mixture was stirred at room temperature for 16 hrs. The reaction was quenched with water (10 mL) and further diluted with dichloromethane (10 mL). The layers were separated and the aqueous layer was further extracted with dichloromethane (2×10 mL). The combined organic layers were washed with brine (10 mL), dried over MgSO$_4$, filtered and concentrated under reduced pressure. The crude material was purified by column chromatography on silica gel using a gradient 0-50% ethyl acetate in heptane as eluent to afford the TBS-protected azido alcohol H (yield: 47%) (where TBS is tert-butyldimethylsilyl) as a colourless oil.

Example 20

Preparation of Hydrochloride Salt

Amino alcohol 1f (500 mg, purity 82.8%) was dissolved in ethyl acetate (3 mL) and a solution of HCl (2.0 M in diethyl ether, 0.65 mL, 1.0 equiv.) was added at room temperature. After stirring for approximately 30 minutes, precipitation started. The suspension was stirred overnight at room temperature, after which the solids were collected by filtration, washed with ethyl acetate (3 mL) and air dried to give hydrochloride 1f' as a yellow solid (390 mg, purity 92.5%).

Example 21

Crystallization of Hydrochloride 1f'

Hydrochloride 1f' (100 mg) from the previous example was dissolved in hot acetonitrile (2 mL). The solution was allowed to cool to room temperature, and solids started to crystallize almost immediately. Stirring was continued for 30 minutes, after which the solids were collected by filtration, washed with acetonitrile (2 mL) followed by heptane (2 mL) and air dried to give hydrochloride 1f' as a light yellow solid (84 mg, purity 96.6%).

Example 22

Preparation of O,O'-Di-p-toluoyl-L-tartaric acid (DPTTA) salt 1f''

Amino alcohol 1f (10.0 g, purity 97.99%) was dissolved in acetonitrile (100 mL) and filtered through a Celite (5 g) pad, which was then washed with additional acetonitrile (50 mL). The combined filtrates were cooled to 0° C., and a solution of (−)-O,O'-Di-p-toluoyl-L-tartaric acid (9.6 g) in acetonitrile (150 mL) was slowly added with vigorous agitation. A milky suspension was formed, which was agitated overnight at 0° C., after which the solids were collected by filtration, washed with acetonitrile (50 mL), MTBE (50 mL) and then air dried to give salt 1f'' as a white solid (16.0 g, purity 99.34%).

Embodiments

1. The salt of formula 1':

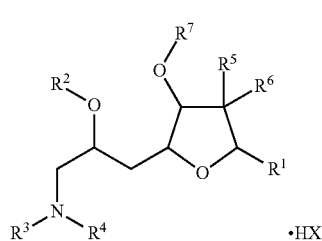

wherein, $R^1$ is —$CH_2$—$CH$=$CR^8R^{8'}$, —$CH_2$—$C$(=$O$)—$R^9$ or —$CH_2$—$CH_2$—$O$—$R^{10}$, wherein $R^8$ and $R^{8'}$ each independently is H or a hydrocarbon, the hydrocarbon optionally having one or more heteroatoms;

$R^9$ is $OR^{11}$, wherein $R^{11}$ is H or a hydrocarbon, the hydrocarbon optionally having one or more heteroatoms;

$R^{10}$ is H or an alcohol protecting group;

$R^2$ is H or an alcohol protecting group;

$R^3$ and $R^4$ each independently is H, allyl, benzyl or a substituted benzyl group;

or $R^2$ and one of $R^3$ and $R^4$ together form —$C(R^{12})(R^{13})$— and the other $R^3$ and $R^4$ is H, allyl, benzyl or a substituted benzyl group, wherein $R^{12}$ and $R^{13}$ each independently is H or a hydrocarbon, the hydrocarbon optionally having one or more heteroatoms;

one of $R^5$ and $R^6$ is H and the other is —$CH_2OR^{14}$ or —$CH_2SO_2$—Ar, or $R^5$ and $R^6$ taken together form =$CH$—$SO_2$—Ar, wherein $R^{14}$ is H or an alcohol protecting group; and Ar is an aryl group; and $R^7$ is H, $C_{1-3}$ alkyl or $C_{1-3}$ haloalkyl; and HX is an acid.

2. The salt according to embodiment 1, wherein the salt has the stereochemical configuration as shown in formula 1a'

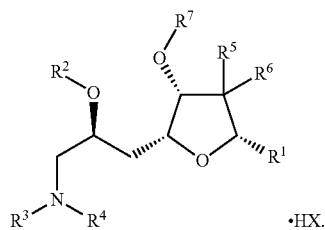

3. The compound according to embodiment 1 or 2, wherein $R^1$ is —$CH_2$—$CH$=$CH_2$, —$CH_2$—$CH$=$CH$—$CH_3$, or —$CH_2$—$CH$=$C(CH_3)_2$.

4. The compound according to any one of embodiments 1 to 3, wherein $R^1$ is

—$CH_2$—$CH$=$CH_2$.

5. The compound according to any one of embodiments 1 to 4, wherein $R^2$ is H, a silyl group, an acyl group or an alkoxycarbonyl group.

6. The compound according to any one of embodiments 1 to 5, wherein $R^3$ and $R^4$ each independently is H, allyl, benzyl or a substituted benzyl group.

7. The compound according to any one of embodiments 1 to 6, wherein one of $R^5$ and $R^6$ is H and the other is —$CH_2SO_2$—Ar.

8. The compound according to any one of embodiments 1 to 6, wherein one of $R^5$ and $R^6$ is H and the other is —$CH_2SO_2$—Ar, and the carbon to which they are attached has the S-configuration.

9. The compound according to any one of embodiments 1 to 8, wherein $R^7$ is a $C_{1-3}$ alkyl group.

10. The compound according to any one of embodiments 1 to 8, wherein $R^7$ is methyl.

11. The compound according to any one of embodiments 1 to 10, wherein the salt formed is a hydrochloric acid salt, sulfuric acid salt, citrate salt, hydrobromic acid salt, hydroiodic acid salt, nitric acid salt, bisulfate salt, phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt (also referred to as mesylic acid salt), ethanesulfonic acid salt, benzenesulfonic acid salt, p-toluenesulfonic acid salt, or a pamoic acid salt (pamoate).

12. The compound according to any one of embodiments 1 to 10, wherein the salt formed is a hydrochloric acid salt, hydrobromic acid salt, sulfuric acid salt, acetic acid salt, O,O'-Di-p-toluoyl-L-tartaric acid salt, phosphoric acid salt, citrate, or methanesulfonic acid salt.

13. The compound according to any one of embodiments 1 to 10, wherein the salt formed is a hydrochloric acid salt or O,O'-Di-p-toluoyl-L-tartaric acid salt.

14. A process for preparation of the salt as defined in any one of embodiments 1 to 13, comprising:

dissolving the compound of formula 1 in an organic solvent; and adding a proton-donating acid to the organic solvent containing the compound of formula 1 to form the salt as defined in any one of embodiments 1 to 13, where the compound of formula 1 is

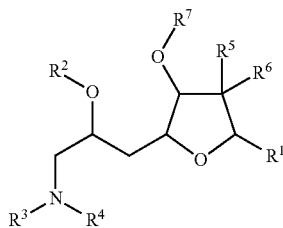

wherein,
R$^1$ is —CH$_2$—CH=CR$^8$R$^{8\prime}$, —CH$_2$—C(=O)—R$^9$ or —CH$_2$—CH$_2$—O—R$^{10}$, wherein
R$^8$ and R$^{8\prime}$ each independently is H or a hydrocarbon, the hydrocarbon optionally having one or more heteroatoms;
R$^9$ is OR$^{11}$, wherein R$^{11}$ is H or a hydrocarbon, the hydrocarbon optionally having one or more heteroatoms;
R$^{10}$ is H or an alcohol protecting group;
R$^2$ is H or an alcohol protecting group;
R$^3$ and R$^4$ each independently is H, allyl, benzyl or a substituted benzyl group;
or R$^2$ and one of R$^3$ and R$^4$ together form —C(R$^{12}$)(R$^{13}$)— and the other R$^3$ and R$^4$ is H, allyl, benzyl or a substituted benzyl group, wherein R$^{12}$ and R$^{13}$ each independently is H or a hydrocarbon, the hydrocarbon optionally having one or more heteroatoms;
one of R$^5$ and R$^6$ is H and the other is —CH$_2$OR$^{14}$ or —CH$_2$SO$_2$—Ar, or R$^5$ and R$^6$ taken together form =CH—SO$_2$—Ar, wherein
R$^{14}$ is H or an alcohol protecting group; and
Ar is an aryl group; and
R$^7$ is H, C$_{1-3}$ alkyl or C$_{1-3}$ haloalkyl.

15. The process according to embodiment 14, wherein the proton-donating acid is added at room temperature.

16. The process according to embodiment 14 or 15, further comprising the step of agitating the solvent after addition of the proton-donating acid.

17. The process according to embodiment 16, wherein agitation is carried out from about 2 to about 48 hours.

18. The process according to any one of embodiments 14 to 17, further comprising the step of filtering the salt as defined in any one of embodiments 1 to 13.

19. The process according to any one of embodiments 14 to 18, further comprising the step of recrystallizing the salt using a second organic solvent.

20. The process according to embodiment 19, wherein recrystallization is carried out by dissolving the salt as defined in any one of embodiments 1 to 13 in the second organic solvent at elevated temperature; allowing the solution to cool permitting crystallization of the salt as defined in any one of embodiments 1 to 13.

21. The process according to embodiment 20, wherein the second organic solvent is a polar aprotic solvent or a polar protic solvent.

22. The process according to embodiment 20, wherein the solvent is ethyl acetate, tetrahydrofuran (THF), dichloromethane (DCM), dimethylformamide (DMF), acetonitrile, propylene carbonate, n-butanol, isopropanol (IPA), n-propanol, ethanol, methanol, toluene, 1,4-dioxane, chloroform, diethyl ether, isopropyl acetate, t-butyl methyl ether or a combination thereof.

23. The process according to embodiments 20, wherein the solvent is ethyl acetate.

24. The process according to any one of embodiments 20 to 23, wherein the elevated temperature is the boiling point of the solution.

25. The process according to any one of embodiments 20 to 23, wherein the elevated temperature is from about 50° C. to about 150° C.

26. The process according to any one of embodiments 20 to 23, wherein the elevated temperature is from about 75° C. to about 120° C.

27. The process according to any one of embodiments 20 to 26, wherein the solution containing the dissolved salt is cooled to room temperature.

28. The process according to any one of embodiments 20 to 26, wherein the solution containing the dissolved salt is cooled to from about −10° to 10° C.

29. The process according to any one of embodiments 20 to 28, further comprising the step of filtering the recrystallized salt.

30. A process for recrystallization of the salt as defined in any one of embodiments 1 to 13, comprising dissolving the salt as defined in any one of embodiments 1 to 13 in a second organic solvent at elevated temperature; allowing the solution to cool permitting crystallization of the salt as defined in any one of embodiments 1 to 13.

31. The process according to embodiment 30, wherein the second organic solvent is a polar aprotic solvent or a polar protic solvent.

32. The process according to embodiment 30, wherein the solvent is ethyl acetate, tetrahydrofuran (THF), dichloromethane (DCM), dimethylformamide (DMF), acetonitrile, propylene carbonate, n-butanol, isopropanol (IPA), n-propanol, ethanol, methanol, toluene, 1,4-dioxane, chloroform, diethyl ether, or isopropyl acetate or a combination thereof.

33. The process according to embodiments 30, wherein the solvent is ethyl acetate.

34. The process according to any one of embodiments 30 to 33, wherein the elevated temperature is the boiling point of the solution.

35. The process according to any one of embodiments 30 to 33, wherein the elevated temperature is from about 50° C. to about 150° C.

36. The process according to any one of embodiments 30 to 33, wherein the elevated temperature is from about 75° C. to about 120° C.

37. The process according to any one of embodiments 30 to 36, wherein the solution containing the dissolved salt is cooled to room temperature.

38. The process according to any one of embodiments 30 to 36, wherein the solution containing the dissolved salt is cooled to from about −10° to 10° C.

39. The process according to any one of embodiments 30 to 38, further comprising the step of filtering the recrystallized salt.

40. A process for preparation of a halichondrin analog, comprising use of the salt as defined in any one of embodiments 1 to 13 or the process as defined in any one of embodiments 14 to 39.

41. A process for preparation of eribulin, comprising use of the salt as defined in any one of embodiments 1 to 13 or the process as defined in any one of embodiments 14 to 39.

42. The compound of formula 1a"

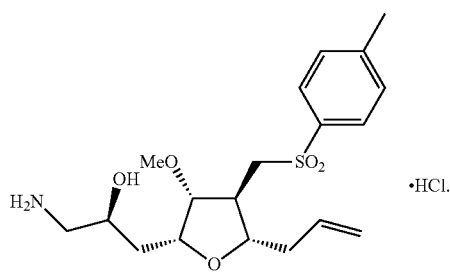

43. The compound of formula 1a*

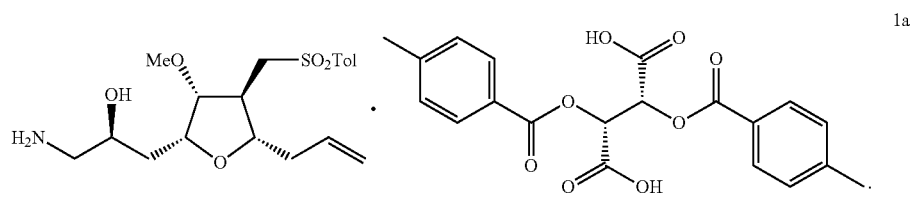

Certain adaptations and modifications of the described embodiments can be made. Therefore, the above discussed embodiments are considered to be illustrative and not restrictive.

What is claimed is:
1. The salt of formula 1':

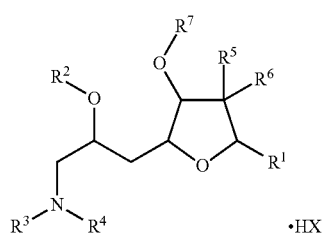

wherein, $R^1$ is —$CH_2$—CH=$CR^8R^{8'}$, —$CH_2$—C(=O)—$R^9$ or —$CH_2$—$CH_2$—O—$R^{10}$, wherein $R^8$ and $R^{8'}$ each independently is H or a hydrocarbon, the hydrocarbon optionally having one or more heteroatoms;

$R^9$ is $OR^{11}$, wherein $R^{11}$ is H or a hydrocarbon, the hydrocarbon optionally having one or more heteroatoms;

$R^{10}$ is H or an alcohol protecting group;

$R^2$ is H or an alcohol protecting group;

$R^3$ and $R^4$ each independently is H, allyl, or benzyl;

or $R^2$ and one of $R^3$ and $R^4$ together form —C($R^{12}$)($R^{13}$)— and the other $R^3$ and $R^4$ is H, allyl, or benzyl, wherein $R^{12}$ and $R^{13}$ each independently is H or a hydrocarbon, the hydrocarbon optionally having one or more heteroatoms;

one of $R^5$ and $R^6$ is H and the other is —$CH_2OR^{14}$ or —$CH_2SO_2$—Ar, or $R^5$ and $R^6$ taken together form =CH—$SO_2$—Ar, wherein $R^{14}$ is H or an alcohol protecting group; and Ar is an aryl group; and $R^7$ is H, $C_{1-3}$ alkyl or $C_{1-3}$ haloalkyl; and HX is hydrochloric acid or O,O'-Di-p-toluoyl-L-tartaric acid.

2. The salt according to claim 1, wherein the salt has the stereochemical configuration as shown in formula 1a'.

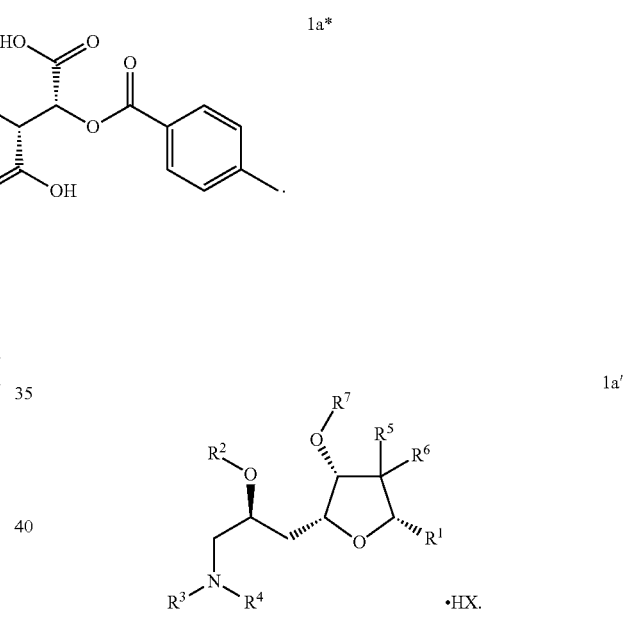

3. The compound according to claim 1, wherein $R^1$ is —$CH_2$—CH=$CH_2$, —$CH_2$—CH=CH—$CH_3$, or —$CH_2$—CH=C($CH_3$)$_2$.

4. The compound according to claim 1, wherein $R^1$ is —$CH_2$—CH=$CH_2$.

5. The compound according to claim 1, wherein $R^2$ is H, a silyl group, an acyl group or an alkoxycarbonyl group.

6. The compound according to claim 1, wherein $R^3$ and $R^4$ each independently is H, allyl, or benzyl.

7. The compound according to claim 1, wherein one of $R^5$ and $R^6$ is H and the other is —$CH_2SO_2$—Ar.

8. The compound according to claim 1, wherein one of $R^5$ and $R^6$ is H and the other is —$CH_2SO_2$—Ar, and the carbon to which they are attached has the S-configuration.

9. The compound according to claim 1, wherein $R^7$ is a $C_{1-3}$ alkyl group.

10. The compound according to claim 1, wherein $R^7$ is methyl.

11. A process for preparation of the salt as defined in claim 1, comprising:
dissolving the compound of formula 1 in an organic solvent; and adding a proton-donating acid to the organic solvent containing the compound of formula 1 to form the salt, where the compound of formula 1 is

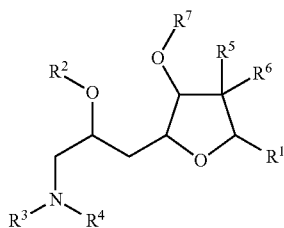

wherein,
R$^1$ is —CH$_2$—CH=CR$^8$R$^{8'}$, —CH$_2$—C(=O)—R$^9$ or —CH$_2$—CH$_2$—O—R$^{10}$, wherein
  R$^8$ and R$^{8'}$ each independently is H or a hydrocarbon, the hydrocarbon optionally having one or more heteroatoms;
  R$^9$ is OR$^{11}$, wherein R$^{11}$ is H or a hydrocarbon, the hydrocarbon optionally having one or more heteroatoms;
  R$^{10}$ is H or an alcohol protecting group;
R$^2$ is H or an alcohol protecting group;
R$^3$ and R$^4$ each independently is H, allyl, or benzyl;
or R$^2$ and one of R$^3$ and R$^4$ together form —C(R$^{12}$)(R$^{13}$)— and the other R$^3$ and R$^4$ is H, allyl, or benzyl, wherein R$^{12}$ and R$^{13}$ each independently is H or a hydrocarbon, the hydrocarbon optionally having one or more heteroatoms;
one of R$^5$ and R$^6$ is H and the other is —CH$_2$OR$^{14}$ or —CH$_2$SO$_2$—Ar, or R$^5$ and R$^6$ taken together form =CH—SO$_2$13 Ar, wherein
  R$^{14}$ is H or an alcohol protecting group; and
  Ar is an aryl group; and
R$^7$ is H, C$_{1-3}$ alkyl or C$_{1-3}$ haloalkyl.

12. The process according to claim 11, wherein the proton-donating acid is added at room temperature.

13. The process according to claim 11, further comprising the step of agitating the solvent after addition of the proton-donating acid.

14. The process according to claim 13, wherein agitation is carried out from about 2 to about 48 hours.

15. The process according to claim 11, further comprising the step of filtering the salt.

16. The process according to claim 11, further comprising the step of recrystallizing the salt using a second organic solvent.

17. The process according to claim 16, wherein recrystallization is carried out by dissolving the salt in the second organic solvent at elevated temperature; allowing the solution to cool permitting crystallization of the salt.

18. The process according to claim 17, wherein the second organic solvent is a polar aprotic solvent or a polar protic solvent.

19. The process according to claim 17, wherein the solvent is ethyl acetate, tetrahydrofuran (THF), dichloromethane (DCM), dimethylformamide (DMF), acetonitrile, propylene carbonate, n-butanol, isopropanol (IPA), n-propanol, ethanol, methanol, toluene, 1,4-dioxane, chloroform, diethyl ether, isopropyl acetate, t-butyl methyl ether or a combination thereof.

20. The process according to claims 17, wherein the solvent is ethyl acetate.

21. The process according to claim 17, wherein the elevated temperature is the boiling point of the solution.

22. The process according to claim 17, wherein the elevated temperature is from about 50° C. to about 150° C.

23. The process according to claim 17, wherein the elevated temperature is from about 75° C. to about 120° C.

24. The process according to claim 17, wherein the solution containing the dissolved salt is cooled to room temperature.

25. The process according to claim 17, wherein the solution containing the dissolved salt is cooled to from about −10° to 10° C.

26. The process according to claim 17, further comprising the step of filtering the recrystallized salt.

27. A process for recrystallization of the salt as defined in claim 1, comprising dissolving the salt in a second organic solvent at elevated temperature; allowing the solution to cool permitting crystallization of the salt.

28. The process according to claim 27, wherein the second organic solvent is a polar aprotic solvent or a polar protic solvent.

29. The process according to claim 27, wherein the solvent is ethyl acetate, tetrahydrofuran (THF), dichloromethane (DCM), dimethylformamide (DMF), acetonitrile, propylene carbonate, n-butanol, isopropanol (IPA), n-propanol, ethanol, methanol, toluene, 1,4-dioxane, chloroform, diethyl ether, or isopropyl acetate or a combination thereof.

30. The process according to claims 27, wherein the solvent is ethyl acetate.

31. The process according to claim 27, wherein the elevated temperature is the boiling point of the solution.

32. The process according to claim 27, wherein the elevated temperature is from about 50° C. to about 150° C.

33. The process according to claim 27, wherein the elevated temperature is from about 75° C. to about 120° C.

34. The process according to claim 27, wherein the solution containing the dissolved salt is cooled to room temperature.

35. The process according to claim 27, wherein the solution containing the dissolved salt is cooled to from about −10° to 10° C.

36. The process according to claim 27, further comprising the step of filtering the recrystallized salt.

37. The compound of formula 1"

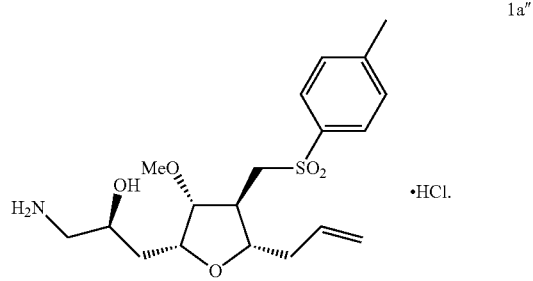 [SMILES: C=CC[C@@H]1O[C@H](C[C@H](O)CN)[C@H](OC)[C@H]1CS(=O)(=O)c1ccc(C)cc1 ; "·HCl."]

38. The compound of formula 1a*
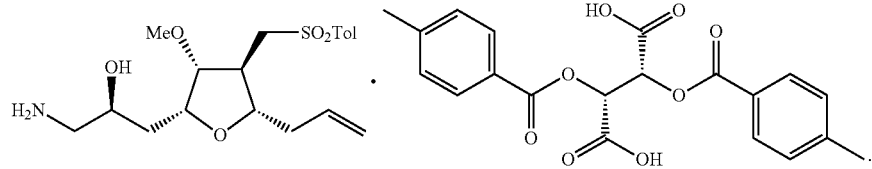
* * * * *